US011904098B2

(12) United States Patent
Westermark et al.

(10) Patent No.: US 11,904,098 B2
(45) Date of Patent: Feb. 20, 2024

(54) ADDITIVE GAS DELIVERY APPARATUS WITH BACKUP

(71) Applicant: INOSYSTEMS, Antony (FR)

(72) Inventors: Magnus Westermark, Sollentuna (SE); Lars-Erik Nilsson, Arsta (SE)

(73) Assignee: INOSYSTEMS, Antony (FR)

( * ) Notice: Subject to any disclaimer, the term of this patent is extended or adjusted under 35 U.S.C. 154(b) by 612 days.

(21) Appl. No.: 15/535,878

(22) PCT Filed: Dec. 19, 2014

(86) PCT No.: PCT/EP2014/078891
§ 371 (c)(1),
(2) Date: Jun. 14, 2017

(87) PCT Pub. No.: WO2016/096056
PCT Pub. Date: Jun. 23, 2016

(65) Prior Publication Data
US 2017/0348503 A1 Dec. 7, 2017

(51) Int. Cl.
*A61M 16/12* (2006.01)
*A61M 16/00* (2006.01)
(Continued)

(52) U.S. Cl.
CPC ........ *A61M 16/12* (2013.01); *A61M 16/0078* (2013.01); *A61M 16/024* (2017.08);
(Continued)

(58) Field of Classification Search
CPC .. A61M 16/12; A61M 16/085; A61M 16/024; A61M 16/0078; A61M 16/104;
(Continued)

(56) References Cited

U.S. PATENT DOCUMENTS 5,558,083 A * 9/1996 Bathe .................... A61M 16/12
128/203.12
5,752,504 A * 5/1998 Bathe .................... A61M 16/12
128/203.12
(Continued)

FOREIGN PATENT DOCUMENTS

WO WO-2014/159912 A1 10/2014

OTHER PUBLICATIONS

Office Action dated Aug. 27, 2019 for Japanese Patent Application No. 2017-531667.

*Primary Examiner* — Kendra D Carter
*Assistant Examiner* — Arielle Wolff
(74) *Attorney, Agent, or Firm* — ArentFox Schiff LLP

(57) ABSTRACT

An additive gas delivery apparatus for delivery of additive gas to inspirational gas can be set to deliver the additive gas according to a dosing setting in normal therapy, and can be set to deliver according to a backup dosing setting in response disruption of signals representing data for controlling the delivery of additive gas according to the dosing setting in normal therapy. An additive gas delivery apparatus has an inlet for the additive gas and an integrated inlet for gas for oxygenating the patient that are connected to a backup line to mix the additive gas and gas for oxygenating the patient to a set concentration of additive gas in the gas mixture at an integrated backup outlet of the additive gas delivery apparatus.

8 Claims, 2 Drawing Sheets

(51) Int. Cl.
*A61M 16/08* (2006.01)
*A61M 16/10* (2006.01)
*A61M 16/16* (2006.01)

(52) U.S. Cl.
CPC ........ *A61M 16/085* (2014.02); *A61M 16/104* (2013.01); *A61M 16/16* (2013.01); *A61M 2016/003* (2013.01); *A61M 2016/0039* (2013.01); *A61M 2016/102* (2013.01); *A61M 2016/1035* (2013.01); *A61M 2202/0275* (2013.01); *A61M 2205/16* (2013.01); *A61M 2205/3334* (2013.01); *A61M 2205/50* (2013.01); *A61M 2205/505* (2013.01)

(58) Field of Classification Search
CPC ........... A61M 16/16; A61M 2016/003; A61M 2016/0039; A61M 2016/102; A61M 2016/1035; A61M 2202/0275; A61M 2205/16; A61M 2205/3334; A61M 2205/50; A61M 2205/505
See application file for complete search history.

(56) References Cited

U.S. PATENT DOCUMENTS

| | | | |
|---|---|---|---|
| 6,089,229 A * | 7/2000 | Bathe | A61M 16/12 128/203.12 |
| 2005/0172966 A1* | 8/2005 | Blaise | A61M 16/12 128/204.21 |
| 2006/0225737 A1* | 10/2006 | Iobbi | A61M 16/026 128/204.22 |
| 2007/0125377 A1 | 6/2007 | Heinonen et al. | |
| 2007/0144515 A1* | 6/2007 | Stenzler | A61M 16/024 128/203.25 |
| 2013/0192595 A1* | 8/2013 | Tolmie | A61M 16/024 128/203.14 |
| 2014/0127081 A1 | 5/2014 | Fine et al. | |

* cited by examiner

ADDITIVE GAS DELIVERY APPARATUS WITH BACKUP

BACKGROUND OF THE INVENTION

Field of the Invention

The present invention relates to an additive gas delivery apparatus for delivery of additive gas to inspirational gas, and which comprises backup delivery of the additive gas in various operational situations where normal delivery of additive gas is interrupted or fails.

Description of the Prior Art

In conjunction with respiratory care of a patient provided by means of a breathing apparatus, such as a ventilator or respirator, the physician may sometimes wish to supplement the breathing gas with an additive gas having a desired medical effect on the patient. Nitric oxide (NO), also known as nitrogen monoxide, is an example of such an additive gas.

In small quantities, NO can have several beneficial effects on the pulmonary function of a subject. In particular, NO has a vasodilating effect and prompt supply of NO may be life critical to patients suffering from vascular spasms in the pulmonary capillaries.

When dosing NO to a ventilator patient limb the NO concentration should be uninterrupted to avoid rebound phenomena. The administration module uses flow sensor signals to administer a constant concentration independent of the flow. An interruption or uncontrolled delivery of NO to the patient can be life threatening. Interruption of delivery of NO may, e.g., be caused by a failure of the administration module. Uncontrolled delivery of NO may be caused by interruption or failure of flow sensor signals.

U.S. Pat. No. 5,558,083 Datex Ohmeda discloses a system having a flow sensor for the administration of NO. The document discusses the addition of O2 gas in case too low oxygen levels are detected. However, no solution is provided for interrupted or uncontrolled administration of NO delivery, which may be a risk for the patient.

The delivery system INOmax DS$_{IR}$® by IKARIA® is an administration module for NO delivery. The module operates using an external flow sensor and injector module for adding the NO gas to the inspiratory gas from the breathing apparatus. In case the delivery system does go into shutdown, it has an integrated backup function which provides a fixed flow of NO gas into the injector module using a manual pneumatic on/off switch and a restrictor built into the delivery side of the system. The backup is only for short term use until a replacement delivery system can be obtained. However, the interruption of NO delivery is critical, even an interruption for a few minutes may be life threatening to the patient. Thus, also this system may have patient risks in view of, e.g., the manual switching of the backup system as well as having a single fixed flow of NO gas for all patient types regardless of the amount of NO gas being administered before the failure. In case of complete electrical failure or failure of the breathing apparatus, the delivery of inspirational gas may be interrupted and the amount of NO to the patient uncontrolled. Furthermore, the backup system can be connected to a resuscitator bag, wherein the same NO gas lines and connections for mixing the NO gas and the inspirational gas from the breathing apparatus are used. When using the resuscitator bag the operator needs to control the NO administration module at the same time as the inspirational gas from the breathing apparatus, such as from a wall connection. In such situations, the operator has to manually administer the amount of inspiration gas to be mixed with the NO in order to not set a too high NO delivery, again leading to patient safety risks.

As mentioned above, unintentional non-delivery of NO to a patient in need of NO therapy is a potentially life-threatening situation. To avoid such situations there is thus a need for a safer and more user-friendly NO delivery system. The present invention addresses a widely recognized need to provide safer additive gas delivery, and thus provides for improved patient safety and/or efficacy of the delivery of additive gas.

SUMMARY OF THE INVENTION

Accordingly, embodiments of the present invention preferably seek to mitigate, alleviate or eliminate one or more deficiencies, disadvantages or issues in the art, such as the above-identified, singly or in any combination by providing an additive gas delivery apparatus, a system including such an apparatus, and a method for monitoring delivery of additive gas.

According to an aspect of the invention, an additive gas delivery apparatus for delivery of additive gas to inspirational gas to be delivered to a patient comprises a gas administration unit having a user interface for entering a dosing setting for the additive gas; a control unit (processor) configured to determine a dose of the additive gas to be added to the inspirational gas based on at least one monitored signal representing a monitored parameter of an inspiratory gas flow of said inspirational gas to said patient and said dosing setting; at least one input for receiving a signal representing a value of said at least one monitored parameter and being connected to the control unit. The control unit is configured to determine at least one of the presence of the signal representing said value of the monitored parameter and the value of the monitored parameter being within a range of valid values. Also, the control unit is configured to switch the dosing setting of the additive gas to a backup dosing setting in response to determining disruption of signals representing a value of said at least one monitored parameter or the value of the monitored parameter being outside the range of valid values.

The additive gas delivery apparatus may comprise a flow sensor for sensing an inspiratory gas flow from a breathing apparatus, and which is configured to provide said signal representing said monitored parameter. Alternatively, the additive gas delivery apparatus may comprise an input configured to receive the signal representing the monitored parameter from a breathing apparatus. The monitored parameter may be a flow of an inspiratory gas, such as from the breathing apparatus. The control unit may be configured to sense a disruption of signals representing said flow of inspiratory gas, or values of said flow of inspiratory gas outside a range of valid flow values.

The control unit may be configured to set the dosing setting of the additive gas to said backup dosing setting based on at least one of a constant flow of an inspiratory gas, patient type, and flow sensor type. The control unit may be configured to switch to a backup dosing setting that is constant.

The control unit may be configured to switch to a backup dosing setting that is a regulated dosing setting based on a measured concentration of the additive gas in a gas mixture of inspirational gas and additive gas.

The additive gas delivery apparatus may comprise a sample line connectable to an inspiratory line from the breathing apparatus downstream of an additive gas outlet to be connected to the inspiratory line. The additive gas delivery apparatus may also comprise at least one sensor may be configured to sense the concentration of the additive gas from a sample of the inspirational gas mixed with the additive gas. The control unit may be configured to set the dosing setting of the additive gas to the backup dosing setting in response to the concentration being outside a range of valid values of concentration.

The control unit may be configured to set the backup dosing setting of the additive gas to a dosing setting determined based on at least one of the average dose delivered during a predetermined number of patient inspirations and a sensed value of the monitored parameter after initiation of the backup dosing setting.

The additive gas delivery apparatus may comprise a first sensor input for receiving the signal representing the monitored parameter, which is an inspiratory gas flow from a breathing apparatus, and a second sensor input for connection to a sample line connectable to a inspiratory line from the breathing apparatus downstream of an additive gas outlet to be connected to the inspiratory line. The second sensor input may be connected to a gas analyzer configured to sense a concentration of the additive gas from a sample of the inspirational gas mixed with the additive gas. The control unit may be configured to first set the dosing setting of the additive gas to a predetermined backup dosing setting based on a constant flow of inspirational gas from the breathing apparatus for a first set of inspirations, and then increase the dosing setting until a desired concentration indicated by a signal received at the second sensor input is reached.

The at least one monitored parameter may comprise a concentration of NO gas in a mix of the inspirational gas and the additive gas, and said range of valid values may be a range of NO concentrations in said mixed gas, preferably 1-40 ppm.

According to another aspect of the invention, a gas delivery system comprises a breathing apparatus connectable to a patient via a breathing apparatus circuit and configured to provide breathing gas to said patient via an inspiratory line of said breathing apparatus circuit; and an additive gas delivery apparatus configured to be detachably connected to said inspiratory line and to deliver additive gas into the breathing gas within said inspiratory line for subsequent delivery of an additive gas containing breathing gas mixture to said patient. The additive gas delivery apparatus is an additive gas delivery apparatus according to embodiments of the invention.

According to another aspect of the invention, a method for monitoring delivery of additive gas to a patient by means of an additive gas delivery apparatus comprises receiving a signal representing a value of at least one monitored parameter at a control unit configured to determine a dose of the additive gas to be added to the inspirational gas based on at least one monitored signal representing a monitored parameter of an inspiratory gas flow of said inspirational gas to said patient; determining at least one of the presence of the signal representing said value of the monitored parameter and the value of the monitored parameter being within a range of valid values; and switching the dosing setting of the additive gas to a backup dosing setting in response to determining disruption of signals representing a value of said at least one monitored parameter or the value of the monitored parameter being outside the range of valid values.

According to another aspect of the invention, a computer-readable storage medium is encoded with programming instructions. The storage medium is loadable into a computerized control system of an additive gas delivery apparatus having a processing unit for receiving a signal representing a value of at least one monitored parameter. The programming instructions cause the computerized control system to execute the method according to embodiments of the invention.

According to another aspect of the invention, an additive gas delivery apparatus for delivery of additive gas to a patient comprises a gas administration module having an additive gas outlet and being configured to provide a dose of the additive gas to the patient based on at least one monitored parameter of a patient inspiratory gas flow in a first operational mode; and a gas backup module for a second operational mode and having an inlet for the additive gas, an integrated inlet for a gas for oxygenating said patient, a backup line, and an integrated backup outlet, the gas backup module being configured to add the additive gas to a patient in case of malfunction of delivery of additive gas from the gas administration module, wherein the inlet for the additive gas and the integrated inlet are connected to the backup line to mix the additive gas and the gas for oxygenating the patient to a set concentration of additive gas in the gas mixture at the integrated backup outlet.

The integrated backup outlet may be connectable to a manual ventilation bag connectable to a patient connection.

The gas backup module may comprise an actuator for switching between the first operational mode and the second operational mode, and wherein the actuator optionally is a mechanic actuator.

The gas backup module may comprise an integrated regulator for regulating a flow of the gas for oxygenation the patient within at least one predetermined range while the additive gas flow is constant.

The gas backup module may comprise a gas flow restrictor in an additive gas line between the first inlet and the backup gas line. The gas flow restrictor may be controllable to set one of a plurality of predetermined gas flows of the additive gas.

A concentration of the additive gas at the integrated gas outlet may be in the range of 1-40 ppm.

The gas backup module may further comprise another integrated backup outlet connected to the inlet for the additive gas but not to the integrated inlet for the gas for oxygenating the patient to provide a flow of additive gas at the other integrated backup outlet.

Some embodiments of the invention provide for a safer and more user-friendly additive gas delivery apparatus for delivery of additive gas, such as NO, to a patient.

Some embodiments of the invention also provide for reduced risk of unintentional non-delivery of additive gas, such as NO gas, to a patient in need of therapy with such additive gas.

Some embodiments provides for more rapidly switching to a backup delivery of additive gas.

The term "comprises/comprising" when used in this specification is taken to specify the presence of stated features, integers, steps or components but does not preclude the presence or addition of one or more other features, integers, steps, components or groups thereof.

DESCRIPTION OF THE PREFERRED EMBODIMENTS

Figure 1:
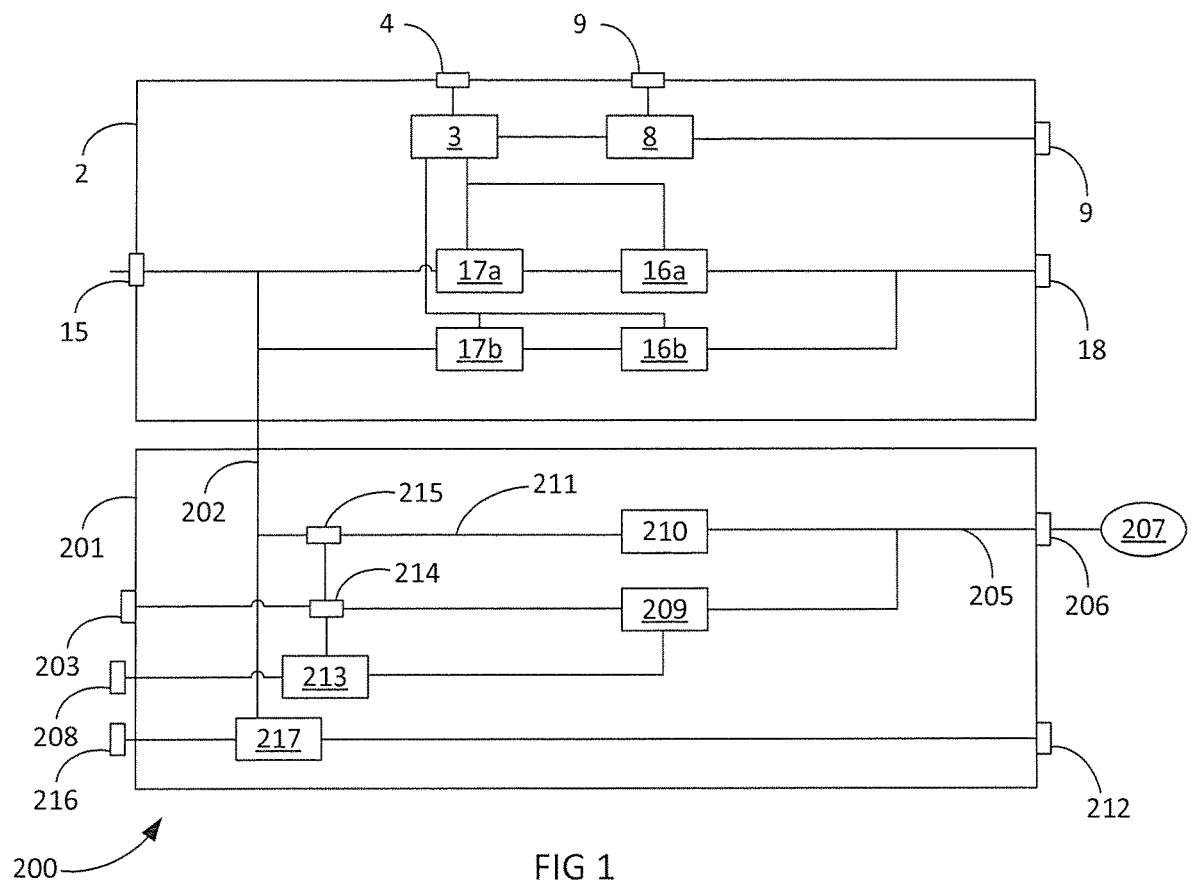
FIG. 1 is a block diagram of the administration module and an additional example backup system.

Specific embodiments of the invention now will be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The present description of the current invention is given with reference to an additive gas delivery apparatus for delivery of additive gas in the form of nitric oxide, NO, as an example only. It should be born in mind, however, that the present invention is not limited strictly to delivery of NO, but can be easily adapted to delivery of other types of additive gas to be delivered to inspirational gas from a breathing apparatus. The additive gas delivery apparatus will hereinafter be referred to as an NO delivery apparatus. In other embodiments not further described in this document, the additive gas delivery apparatus may be configured for delivery of another additive gas having a therapeutic effect on the patient, e.g. carbon oxide. The additive gas delivery apparatus may also be incorporated or connected to a gas delivery system.

In the following, the additive gas delivery system will first be described with reference to FIG. 1, and then the gas delivery system with reference to FIGS. 2-3, followed by a description of a method for monitoring delivery of additive gas to a patient by means of an additive gas delivery apparatus. Finally, an example of an optional backup system will be described with reference to FIG. 1.

FIG. 1 illustrates some embodiments of the NO delivery apparatus 1 for delivery of additive gas to inspirational gas to be delivered to a patient. The NO delivery apparatus 1 comprises gas administration unit 2 having a user interface for entering a dosing setting for the additive gas. The user interface will be further described with reference to FIGS. 2-4 below. The NO delivery apparatus 1 further comprises a control unit 3 configured to determining a dose of the additive gas to be added to the inspirational gas based on at least one signal representing a monitored parameter of an inspiratory gas flow of said inspirational gas to the patient and the dosing setting. The dose may also be determined based on the concentration of the gas in the gas supply for delivery of NO. Available concentrations are normally in the range of 250 ppm to 1000 ppm. The concentration of NO in the gas supply may be indicated by the user interface. A signal representing a value of said at least one monitored parameter may be received at an input 4, which is connected to the control unit 3. The monitored parameter is further described below.

The control unit 3 is configured to determine the presence of the signal representing the value of the monitored parameter. Alternatively or additionally, the control unit 3 is configured to determine if the value of the monitored parameter is within a range of valid values. Furthermore, the control unit 3 is configured to switch the dosing setting of the additive gas to a backup dosing setting in response to determining disruption of signals representing a value of said at least one monitored parameter. Alternatively or additionally, the control unit 3 is configured to switch the dosing setting of the additive gas to a backup dosing setting in response to determining that the value of the monitored parameter is outside the range of valid values. In response to switching to the backup dosing setting, a backup dose will be delivered to the gas delivery system. This may be done automatically, whereby patient safety is increased. The apparatus is also more convenient to operate.

For example, the control unit is configured to switch the dosing setting to the backup dosing setting when any of the following monitored parameters are disrupted, for example disrupted as indicated:

Flow sensor data is not received; signal representing flow sensor data not received, which is an indication of a disrupted signal.

NO concentration too high/low; a signal represents the value of the NO concentration in the gas delivered to the patient. The control unit 3 may determine that the signal indicates a value that is outside a range of valid values.

Flow sensor failure; a first value of the signal may indicate that the flow sensor is ok and operable, which is monitored. A second value of the signal may indicate that the flow sensor is not ok and not operable; the second value indicates a disruption of the monitored parameter, which is the first value.

Loss of operational parameters; availability of operational parameters, such as patient type, flow sensor type, concentration of NO in gas supply, etc. is monitored, such as checked in a memory at regular intervals. A first value of a signal may indicate that the actual values of all the operational parameters that are expected are available. A second value of the signal may indicate that any of the operational parameters is missing, wherein the signal is disrupted when the second value is indicated.

The dosing setting and the backup dosing setting may be entered and/or defined as a concentration, i.e. a concentration of NO in the mix of NO and gas for oxygenating the patient, or a dose, i.e. bolus per inspiration or time unit.

Figure 2:
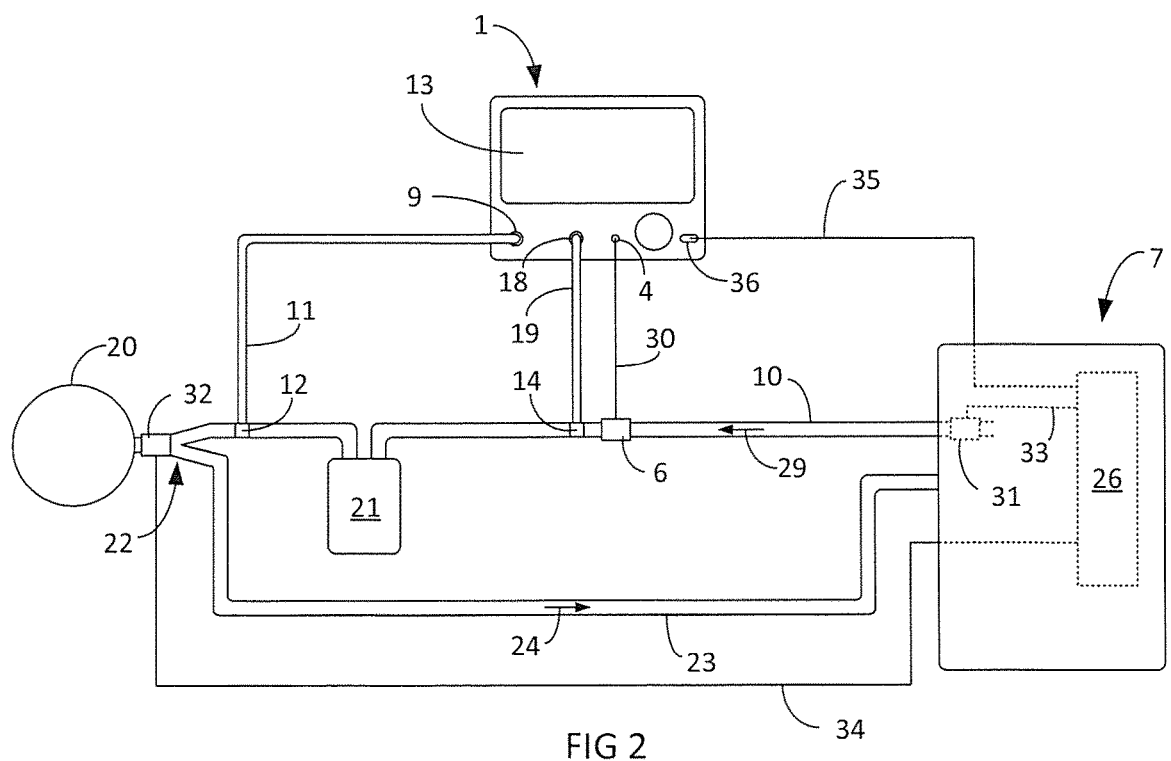
FIG. 2 is a schematic view of a gas delivery system comprising an additive gas delivery apparatus.

In some embodiments, the NO delivery apparatus 1 comprises or is connected to a flow sensor 6 (FIG. 2). The flow sensor 6 is configured to sense an inspiratory gas flow from a breathing apparatus 7. The monitored parameter may be a flow of the inspiratory gas from the breathing apparatus 7. The flow sensor 6 may be configured to provide the signal representing said monitored parameter at the input 4. Alternatively or additionally, the input 4 may be configured to receive the signal representing the monitored parameter from the breathing apparatus 7, such as will be described below. The control unit 3 may be configured to sense a disruption of signals representing said flow of inspiratory gas. Alternatively or additionally, the signals may represent values of said flow of inspiratory gas outside a range of valid flow values. For example, if signals are expected at regular intervals, but no signals have been received with such an interval, it may be determined that a disruption of flow signals has occurred, and the backup dosing setting is initiated. Similarly, if the signal indicates a value that is too high or too low, the backup dosing may be initiated, again leading to patient safety an efficient NO delivery.

In some embodiments, the control unit 3 is configured to set the dosing setting of the NO to the backup dosing setting based on a constant flow of an inspiratory gas from the breathing apparatus. For example, a constant flow of an inspiratory gas may be a bias flow of inspiratory gas. In order to have a minimum amount of NO delivered to the patient, but ensure that the NO concentration is not too high, the dosing is calculated based on the bias flow from the breathing apparatus or a wall connection. Hence, the control unit 3 is configured to switch to a backup dosing setting that is constant, whereby patient safety is ensured. A plurality of constant settings may be applied, such as based on patient type. Since the flow is considered to be constant, the backup dose of delivered NO to the gas delivery system will be constant. The constant flow may be different for different patient types, such as for an adult and a child. Hence, this leads to patient safety to not deliver a too high concentration of NO to the patient, but at the same time a dose is added to the gas delivery system that is adjusted to patient type and thus not lower than necessary for safe delivery. Patient type may be set using the user interface or determined based on type of flow sensor or flow measurement range, as will be described below.

As is illustrated in FIGS. 1-2, in some embodiments the gas administration unit 2 comprises a gas analyzer 8. The gas analyzer 8 is configured to receive a sample of a gas mixture via a gas sample port 9 of the NO delivery apparatus 1. Also, the gas analyzer 8 may be configured to determine the concentration of at least one monitored gas of the mixture of gases, which is a monitored gas parameter. The monitored gas concentration may be at least one of NO, NO2 and O2 concentrations in said gas sample. The gas sample port 9 is connected to an inspiratory line 10 of the breathing apparatus circuit, downstream the point of delivery of NO from the NO delivery apparatus 1, via a gas sample line or conduit 11 detachably connected to the inspiratory line 10 by means of a conduit connector 12. The gas administration unit 2 may further include a flow generator (not shown) configured to generate a flow of gas from the inspiratory line 10 to the gas analyzer 8, via the gas sample line 11 and gas sample port 9. The concentration of the monitored gas parameter in the gas sample is communicated by the gas analyzer 8 as a signal representing the value of the monitored gas parameter to the control unit 3 of the NO delivery apparatus 3. The control unit 3 may receive the signal representing the value of the at least one monitored gas parameter. Hence, the control unit 3 may be configured to switch to a backup dosing setting that is a regulated dosing setting based on a measured concentration of the additive gas.

The control unit 3 is configured to determine presence of the signal representing the value of the at least one monitored gas parameter. Additionally or alternatively, the control unit 3 is configured to determine whether the value of the monitored gas parameter is within a range of valid values. If such signals are disrupted, or the signals indicates values that are out of a range of valid values, the control unit 3 is configured to switch the dosing setting of the additive gas to a backup dosing setting. Furthermore, the control unit 3 may be configured to take actions based on the monitored gas parameter, which actions for example may include display of information related to said concentrations on a screen or touchscreen 13 of the user interface, and activation of an alarm in case of too high or too low NO concentration, too high NO2 concentration or too low O2 concentration. Generating an alarm in case of too low NO concentration downstream the point of delivery of NO in the inspiratory line 10 provides an extra layer of safety allowing the system operator to be alerted also in situations in which no or too low flows of NO is delivered by the NO delivery apparatus 1 when operated in running mode or another active state.

In some embodiments, the gas sample line 11 is connectable to the inspiratory line 10 from the breathing apparatus 7 downstream of an additive gas outlet 14 to be connected to the inspiratory line 10. The gas analyzer 8 is configured to sense the concentration of NO from a sample of the inspirational gas mixed with the additive gas. The control unit 3 is configured to set the dosing setting of NO to the backup dosing setting in response to the concentration being outside a range of valid values of concentration. The additive gas outlet 14 may comprise an injector for injecting the NO gas into the inspiratory gas to mix the gases. Alternatively, the NO gas may be delivered by pulsed NO gas over a flow restrictor, such as will be described below.

In some embodiments, the control unit 3 is configured to set the backup dosing setting of NO to a dosing setting determined based on an average dose delivered during a predetermined number of patient inspirations. The average dosing setting may be initiated when the backup dosing setting is initiated. Then, the monitored parameter, such as the concentration of NO in the gas sample, may be sensed after initiation of the backup dosing setting. The backup dosing setting may then be modulated towards a set concentration. The set concentration may be predetermined based on patient type, or a value input via the user interface. The average dosing setting may be based on tidal volume and frequency. For pressure support, the tidal volumes as well as the frequency will vary. For example, the number of inhalations is in the range of 20-60 per minute and varies depending on patient type, i.e. adult or child/infant. After switching to the backup dosing setting, the dosing setting may be set to a backup setting based on a set value and a fixed flow, for example to a concentration of 20 ppm at a bias flow of inspiratory gas of 2 l/min. The set value may be the dosing setting for the patient in therapy. Then, the backup dosing setting is modulated, by averaging the dose delivered during a predetermined number of patient inspirations, against a dosing setting that is lower than the set value for regular therapy, such as to a concentration of 15 ppm in this example.

In some embodiments, the NO delivery apparatus 1 comprises both a first sensor input, such as input 4, and a second sensor input, such as gas sample port 9, for receiving the gas sample. A sensor, such as the gas analyzer 8, may be configured to sense the concentration of NO from the sample of the inspirational gas mixed with the NO. In such embodiments, the control unit 3 may be configured to first set the dosing setting of NO to a predetermined backup dosing setting based on a constant flow of inspirational gas from the breathing apparatus for a first set of inspirations, and then increase the dosing setting until a desired concentration indicated by a signal is reached. Hence, the desired concentration may be increased also after switching to a backup dosing setting, rather than fixed at a low level with remained control that the dosing setting is not set too high. Still, it is not a closed loop regulation, since the NO concentration may vary within a predefined range in view of a fixed NO flow delivered to a varying flow of inspirational gas. However, the average dose of NO delivered to the gas delivery system will be improved compared to no regulation. Hence, patient safety is ensured while optimizing delivery when running in backup mode.

The control unit 3 may be configured to control the flow of NO delivered into the inspiratory line 10 of the breathing apparatus circuit to obtain a user-selectable, constant concentration of NO in the breathing gas mixture delivered to the patient, typically within the range of 0-80 ppm and normally within the range of 1-40 ppm, such as set in the range of 1-40 ppm via the user interface. The dosing setting and the backup dosing setting may be a setting of a concentration of NO in the gas mix, i.e. a ppm setting, or a dose setting, such as bolus (gram or mole per inhalation) or gram/mole per time unit of NO added to the gas delivery system. The backup dosing setting may be set for a delivery of a fixed concentration, such as 20 ppm, calculated against a bias flow, such as a bias flow of about 2 l/min for an adult or a bias flow of 0.5 l/min for a child, or against an average flow during a predetermined time period before initiation of backup dosing. The concentration of NO in the gas delivered to the patient will be in the range of 5-15 ppm NO for this example, i.e. lower than the calculated concentration, but patient safety is ensured by calculating against the bias flow. If information about patient type or flow sensor type is missing, the backup setting may be set for a delivery of the same amount but for a bias flow between the bias flow for the adult and the bias flow for the child.

The dosing setting and the backup dosing setting may be a setting of an amount, such as volume, which is dependent on the concentration, per time unit.

The monitored parameter may also be NO2 gas, wherein the NO2 concentration in the sample should not exceed predetermined values or ranges, such as 0.5-5 ppm NO2 in the mix of inspiratory gas and additive gas.

For the delivery of the NO gas, the NO delivery apparatus 1 comprises at least one NO gas inlet 15, to which an NO gas supply 25 (FIG. 3), such as an NO gas cylinder, may be connected. In some embodiments, the NO delivery apparatus 1 comprises a plurality of inlets for connecting a plurality of NO gas supplies. Having at least two gas supplies secures that NO may always be delivered, also when one of the supplies is empty. The NO gas inlet 15 is connected to a regulator 16a for regulating the flow of NO gas. The regulator 16a may be connected to a switch 17a, such as a pneumatic switch. In some embodiments, the NO gas delivery apparatus 1 comprises a second regulator 16b connected to the NO gas inlet 15 via a second switch 17b. The control unit 3 is connected to the regulators 16a, 16b and the switches 17a, 17b, and configured to control the switching in/out of flow of NO gas via the switches 17a, 17b, as well as the actual flow of NO gas to provide the actual NO dose as discussed above. The regulators 16a, 16b, are connected to an NO gas outlet port 18 to which the NO gas delivery conduit 19 may be connected for connection to the additive gas outlet 14. Each regulator 16a, 16b may provide a flow of NO, and be controlled by e.g. pulsed delivery of NO gas, and/or constant delivery of NO gas with controlled flow restriction, as is generally known. Each regulator 16a, 16b may comprise a flow restrictor, such as a flow restrictor for fixed flow or a variable orifice valve for variable flow. Furthermore, each regulator 16a, 16b may have a plurality of flow lines such that a different flow is provided in each flow line. Thus, the flow of NO can be modulated by switching to one of the regulators 16a, 16b, and then regulating the flow from the selected regulator 16a, 16b. Hence, delivery based on patient type may be provided also for the backup dosing setting, wherein patient safety and optimized NO delivery is provided.

FIG. 2 illustrates a gas delivery system 1 for providing a mixture of inspirational gas and NO gas to the patient 20. The gas delivery system 1 comprises the additive gas delivery apparatus 1 according to embodiments of the invention. The additive gas delivery apparatus 1 is detachably connected to an inspiratory line 10 of the breathing apparatus circuit to which the patient 20 is connected. The breathing apparatus circuit comprises the breathing apparatus 7, e.g. in form of a ventilator or respirator. The breathing apparatus 7 is arranged to provide ventilatory support to the patient 20 through the supply of breathing gas to the patient 20 via the inspiratory line 10. The breathing gas may comprise oxygen (O2), air or a mixture therebetween but may be any oxygen containing gas mixture suitable for oxygenating the patient. A humidifier 21 may be arranged in the inspiratory line 10 for humidifying a breathing gas mixture before being delivered to the airways of the patient 20. The breathing apparatus circuit further comprises a Y-piece 22 connecting the inspiratory line 10 and the patient 20 to an expiratory line 23 conveying expiration gases away from the patient 20, as indicated by the arrow 24 in the expiratory line 23.

Figure 3:
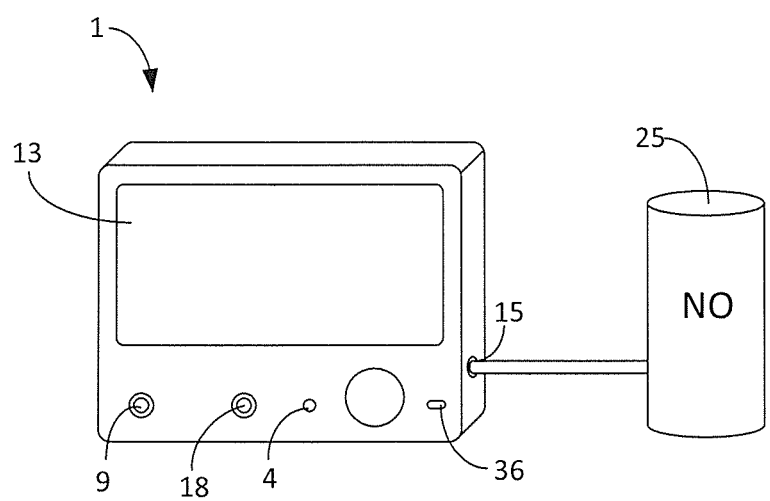
FIG. 3 a schematic view of certain parts and components of the additive gas delivery apparatus of FIGS. 1-2, and an external supply of additive gas to which the additive gas delivery apparatus is connected.

As is illustrated in FIGS. 1 and 3, the NO delivery apparatus 1 may comprise the gas administration unit 2. The gas administration unit 2 comprises the control unit 3 for adapting the flow of pressurized NO received from the NO supply 25 to a suitable flow profile according to which NO is delivered by the NO delivery apparatus 1 via gas outlet 18 of the housing and further via the gas delivery conduit 19 into the inspiratory line 10 for further delivery to the patient 20. To this end, the control unit 3 may be configured to control the delivered dose of NO based on the dosing setting and patient flow measurements. The delivered dose, such as concentration of NO in the mix of inspiratory gas and NO gas, is monitored to verify that the dosing mechanism is operating correctly. In this embodiment, the gas delivery conduit 19 is detachably connected to the inspiratory line 10 of the breathing apparatus circuit by means of a conduit connector at the additive gas outlet 14 constituting said point of delivery of NO into the inspiratory line 10. Thus, the standalone, single unit NO delivery apparatus 1 is detachably connected to an inspiratory line 10 of a breathing apparatus circuit and configured to deliver a flow of NO into a flow of breathing gas in said inspiratory line 10, which flow of breathing gas is provided by a breathing apparatus 7 connected to one end of said inspiratory line 10, for subsequent delivery of an NO containing breathing gas mixture to a patient 20, connected to the other end of said inspiratory line 10. As discussed in the background portion, prompt supply of NO may be life critical e.g. to patients suffering from vascular spasms in the pulmonary capillaries and, therefore, it is of utmost importance that NO therapy is activated without further delay when a patient in need of such therapy is connected to the breathing apparatus circuit. Hence, the NO delivery apparatus comprises backup delivery of NO gas in order to increase patient safety.

The NO delivery apparatus 1 comprises the control unit 3. The control unit 3 is typically realized in form of at least one data processing unit (not shown) configured to execute computer program code stored in form of at least one computer program in at least one non-volatile memory (not shown) of the NO delivery apparatus 1. Unless stated otherwise, functions herein described as being performed by the control unit 3 are performed by said processing unit 3 through execution of said computer program stored in said non-volatile memory of the NO delivery apparatus 1.

As mentioned above with regard to FIG. 1 and further illustrated in FIG. 2, the monitored parameter is typically a parameter relating to a flow and/or pressure, and typically a flow and/or pressure indicative of breathing activity of the patient 20. Said breathing activity may be spontaneous breathing activity caused by the patient 20 itself, or it may be supported or controlled breathing activity partially or fully caused by the breathing apparatus 7 to which the patient is connected to receive ventilatory support. The arrow 29 indicates a flow of breathing gas in the inspiratory line 10 of the breathing apparatus circuit. To monitor said flow, the NO delivery apparatus 1 may comprise the flow sensor 6. The flow sensor 6 is an external flow sensor of the NO delivery apparatus 1, meaning that it is located outside the NO delivery apparatus housing. The flow sensor 6 is configured to be detachably connected to the inspiratory line 10 of the breathing apparatus circuit to monitor the flow therein. Signals representing the flow measurements obtained by the flow sensor 6 may be provided to the control unit 3 via a wired or wireless signaling link 30, which is connected to the input 4.

Alternatively or additionally, the NO delivery apparatus 1 may comprise a communication unit (not shown) configured to communicate with the breathing apparatus 7 and to receive therefrom information related to a flow and/or pressure indicative of breathing activity of the patient 20, which flow and/or pressure is measured by means of a flow and/or pressure sensor of said breathing apparatus 7. For example, the breathing apparatus 7 may be equipped with a flow and/or pressure sensor 31 arranged in an inspiratory part of the breathing apparatus 7 and/or a flow and/or pressure sensor 32 arranged in the Y-piece 22 connecting the inspiratory line 10 and the expiratory line 23 of the breathing apparatus circuit with the patient 20. A flow sensor (not illustrated) may alternatively be provided in the expiratory section of the breathing apparatus. Signals representing flow and/or pressure measurements obtained by said sensors 31, 32 may be communicated to the control unit 26 of the breathing apparatus 7 via sensor links 33, 34 and forwarded to the control unit 3 of the NO delivery apparatus 1 for use as a monitored parameter in the determination of the presence of the signal representing said value of the monitored parameter and the value of the monitored parameter being within a range of valid values. The information related to said flow and/or pressure measurements may be communicated from the breathing apparatus 7 to the NO delivery apparatus 1 via a wired or wireless communication link 35. In some embodiments, the NO delivery apparatus 1 is provided with s serial or parallel communication interface, such as an RS-232 interface 36, and the communication link 35 is an RS-232 communication link.

In general, the system may switch to the backup dosing setting in response to at least one of failure of signals representing flow value, disruption of signal representing flow value, disconnection of sensor for delivery of signal representing flow value, no flow sensor identified. In some embodiments, the control unit 3 is configured to switch to the backup dosing in response to disruption of at least two monitored parameters.

In some embodiments, external flow sensors configured for different flow measurement ranges are used, one flow sensor for adults and another flow sensor for children. This is due to the limited range capacity of most flow sensors. A flow sensor adapted for measurement of the patient flow range of a particular type of patient will give more accurate flow data and thus accurate NO dosing. Sensor type data or sensor measurement flow range data may be communicated to the NO delivery apparatus 1. Hence, the control unit 3 knows whether an adult or child is connected. The backup dosing may thus be set based on flow sensor type, providing for patient safety and optimized delivery of NO. If flow sensor type is not identified, the backup dosing may be set to a backup dosing that is between the backup dosing setting for a flow sensor for an adult and a backup dosing setting for a flow sensor for a child. If communication of signals representing flow data is disrupted, NO concentration is too high or any other indication of failure of data or delivery, the dosing setting may be set to the fixed dosing setting dependent on the flow sensor type. In the absence of flow measurement range/patient type data, a mid-setting may be set, which is between the backup dosing setting for an adult and the backup dosing setting for a child.

The patient type may be set via the user interface including the touchscreen 13, e.g. if not possible to determine from the sensor type. Also, the backup dosing setting of NO may be manually set by the operator by manually entering the setting via the screen/touchscreen 13.

Figure 4:
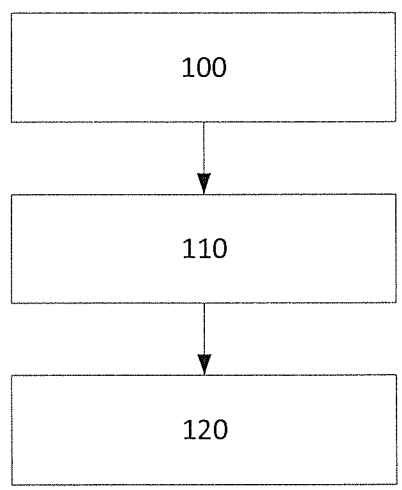
FIG. 4 is a flowchart illustrating a method for monitoring delivery of additive gas.

FIG. 4 illustrates a method for monitoring delivery of NO to a patient by means of an additive gas delivery apparatus. In a step 100, a signal representing a value of at least one monitored parameter is received at the control unit 3, which is configured to deteiiine the dose of the NO gas to be added to the inspirational gas based on at least one monitored signal representing a monitored parameter of an inspiratory gas flow of inspirational gas to the patient 20 and a dosing setting. In a step 110, the presence of the signal representing the value of the monitored parameter is determined. Alternatively or additionally, the value of the monitored parameter being within a range of valid values is determined. In a step 120, the dosing setting of NO is switched to a backup dosing setting in response to determining disruption of signals representing a value of said at least one monitored parameter and/or the value of the monitored parameter being outside the range of valid values.

FIG. 1 illustrates an optional backup system 200 for backup delivery of additive gas of the type disclosed above. In some embodiments the NO delivery apparatus 1 comprises the gas administration unit 2 configured to switch to a backup delivery, such as described above, in combination with the backup system 200. In other examples, the NO delivery apparatus comprises only backup system 200.

Backup system 200 comprises a gas administration module having an additive gas outlet and being configured to provide a dose of the additive gas to the patient in a first operational mode. The gas administration module may be configured according to the embodiments of gas administration module 2 described above with regard to FIGS. 1-4. The backup system 200 further comprises a gas backup module 201 for a second operational mode. The gas backup module 201 has an inlet 202 for NO. Inlet 202 may be connected to NO gas inlet 15 and NO gas supply 25. The gas backup module 201 further has an integrated inlet 203 for a gas for oxygenating said patient, a backup line 205, and an integrated backup outlet 206. The gas backup module 200 is configured to add NO to a patient in case of malfunction of delivery from the gas administration module, such as gas administration module 2. The inlet 202 for the NO gas and the integrated inlet 203 are connected to the backup line 205 to mix NO and the gas for oxygenating the patient to a set concentration of additive gas in the gas mixture at the integrated backup outlet 206.

The integrated inlet 203 for a gas for oxygenating said patient may be connected to a gas cylinder or to a wall mounted gas outlet for such gas.

The integrated backup outlet 206 may be connected to a manual ventilation bag 207 connectable to a patient connection, such as an intubation tube, a face mask, nasal interface etc.

The gas backup module 201 may comprise an actuator 208 for switching between the first operational mode and the second operational mode. The actuator 208 may be a mechanic and/or pneumatic actuator.

The gas backup module 200 may comprise an integrated regulator 209 for regulating a flow of the gas for oxygenation the patient within at least one predetermined range while the NO gas flow is constant.

The gas backup module 200 may comprise a gas flow restrictor 210 in an additive gas line 211 between the inlet 202 for NO and the backup gas line 205. The gas flow restrictor 210 may be controllable to set one of a plurality of predetermined gas flows of the additive gas, such as based on patient type. In some embodiments, the gas flow restrictor 210 may comprise a plurality of interchangeable orifices for different flows, whereby it may be controlled by selecting a desired orifice for a desired flow. In other embodiments, the gas flow restrictor comprises a variable orifice with a variable flow that can be controlled to set the desired flow.

The gas backup module 200 may comprise another integrated backup outlet 212 connected to the inlet 202 for the NO gas but not the integrated inlet 203 for the gas for oxygenating the patient to provide a flow of additive gas at the other integrated backup outlet 212.

The concentration of the additive gas in the gas mixture at the integrated gas outlets 206 may be within the ranges of 1-40 ppm depending on the concentration of the gas in the gas supply 35. The concentration at outlet 212 has a concentration corresponding to the concentration in the gas supply 25.

The actuator 208 may be connected to a first controller 213, which is configured to control flow of NO gas and flow of gas for oxygenating the patient. The first controller 213 may control a first switch 214 in a gas line for the gas for oxygenating the patient between the integrated inlet 203 and the integrated regulator 209. The first controller 213 may control a second switch 215 in the additive gas line 211 between the inlet 202 for the NO gas and the gas flow restrictor 210. Furthermore, the first controller 213 is connected to the integrated regulator 209 and configured to control the flow of gas for oxygenating the patient. The first controller 213 and the switches 214, 215 may comprise at least one pneumatic switch switching in/out of a gas flow, such as a valve.

A second actuator 216 may be connected to a second controller 217. The second controller may be connected to the inlet 202 for the NO gas and the other integrated backup outlet 212. The second controller 216 may comprise a switch or regulator, such as a pneumatic or electronic switch or regulator that may regulate the flow of NO gas to the other integrated outlet 212.

The first actuator 208 and/or the second actuator 216 may comprise a flow meter, such as a rotameter, with a regulator for regulating the flow of gas. Hence, using the system according to embodiments of the invention, the operator only needs to control the NO delivery apparatus in case of emergency backup of NO gas is needed, wherein patient safety is increased compared to prior systems which do not have delivery of gas for oxygenating the patent integrated. In such prior systems, the regulation of gas for oxygenating the patent is located outside of the NO delivery apparatus, sometimes outside reach from the apparatus. Hence, in emergency situations where hand-bagging is necessary, such as during power failure, the operator may administer gas for oxygenating the patient as well as NO only from the NO delivery apparatus. In the present example, a dual-scale may be provided at the flow meter, which indicates amount of NO delivered for a particular flow of gas for oxygenating the patient. Hence, the concentration of NO in the gas delivered to the patient may be controlled by regulating the flow of gas for oxygenating the patient, wherein backup administration of NO gas is more convenient for the operator and safer for the patient.

Hence, using the backup system 200, in case of power failure or other malfunctioning, the NO delivery apparatus can be set into backup mode. A constant basal dose can be mixed with gas for oxygenating the patient and administrated by hand bagging using the manual ventilation bag 207 or via a nasal/face mask interface for patients capable of breathing without support. The integrated backup outlet 206 allows for switching to a different NO delivery apparatus as well as to hand-bagging quicker than not having such an integrated outlet. The manual ventilation bag 207 can be directly connected to the backup outlet 206 and to the patient without having to disconnect any other connections of the system, again leading to improved patient safety.

The actuators 208, 216 may be operated manually by turning from closed to open position in order to activate the backup system 200. This will start gas for oxygenating the patient flowing from a cylinder connected to the integrated inlet 203. The first controller 213 may comprise a valve provided with a micro-switch that indicates its position to the main system to notify the operator that gas administration in the first mode as well as gas administration in the second mode are operative. Hence, if power is available an indication of the presently active mode may be provided on the user interface. The pressure of the gas for oxygenating the patient may be measured by a gauge pressure sensor and an alarm may be issued if the pressure drops below a threshold when setting up the NO delivery apparatus for therapy. The pressure of the gas for oxygenating the patient may be reduced by integrated regulator 209, which may comprise a manually adjustable pressure regulator feeding a variable orifice metering valve, which facilitates adjustment of the flow of gas for oxygenating the patient, such as from about 5 to about 20 liter/min. The actual flow may be indicated by a flow meter, such as a rotameter. The pressure of the gas for oxygenating the patient after switch 214 may open switch and regulator unit 215 letting NO gas flow from the NO cylinder, such as from the cylinder having the highest pressure in case two cylinders of NO are available. Check valves (not shown) in case of multiple gas supplies may be provided at the inlet 202 to ascertain that no NO gas will flow into the NO cylinder with lowest pressure or to atmosphere in case a second cylinder is not connected. Should the cylinder with gas for oxygenating the patient run out of gas, switch 215 may automatically close to prevent administration of excessively high levels of NO to the patient. Hence, patient safety is ensured. The pressure of the NO gas may be reduced by manual regulator (not shown). A constant flow of NO may be generated by an orifice of the switch and regulator unit 215. A flow indicator of the gas flow restrictor 210 may indicate the presence of an NO flow to the operator. The flow indicator of the gas flow restrictor 210 may be a simplified flow meter, such as a simplified rotameter. The flow of gas for oxygenating the patient and the NO flow are mixed in the backup system 200 and fed to the integrated outlet 206. The integrated outlet 206 may be connected to a manual ventilation bag to allow for hand bagging of the patient.

Since the flow of gas for oxygenating the patient can be adjusted while the NO flow is constant, the NO concentration can be adjusted by the oxygen flow. For example, the backup system 200 may therefore deliver an NO concentration of 8-32 ppm for 800 ppm cylinder and 4.5-18 ppm for a 450 ppm cylinder.

$$Q_{O2}(C_{pat}) = \frac{Q_{NO}}{C_{pat}}(C_{cyl} - C_{pat})$$

$Q_{NO}$=fixed volumetric NO flow,
$C_{pat}$=desired NO concentration in patient gas, ppm v/v
$C_{cyl}$=NO concentration in cylinder
$Q_{O2}(C_{pat})$=volumetric O2 flow to yield $C_{pat}$ The oxygen delivered to the patient will be somewhat diluted by the NO/N2 mixture added. Thus the concentration of gas for oxygenating the patient, such as oxygen, may be 96% to 99% in case the supply of gas for oxygenating the patient is 100% oxygen gas. Ambient pressure may influence performance of the backup system 200, as is generally known.

An additive gas delivery apparatus comprising the backup system 200 may be provided in combination with a breathing apparatus, which is connectable to a patient via a breathing apparatus circuit and configured to provide breathing gas to said patient via an inspiratory line of said breathing apparatus circuit.

It should also be appreciated that features disclosed in the foregoing description, and/or in the foregoing drawings and/or following claims both separately and in any combination thereof, be material for realizing the present invention in diverse forms thereof. When used in the following claims, the terms "comprise", "include", "have" and their conjugates mean, "including but not limited to".

The present invention has been described above with reference to specific embodiments. However, other embodiments than the above described are equally possible within the scope of the invention. Different method steps than those described above may be provided within the scope of the invention. The different features and steps of the invention may be combined in other combinations than those described. The scope of the invention is only limited by the appended patent claims.

The invention claimed is:

1. An additive gas delivery apparatus for delivery of additive gas to a patient, comprising:
   a gas administration module having an additive gas outlet and being configured to provide a dose of the additive gas to the patient based on at least one monitored parameter of a patient inspiratory gas flow in a first operational mode; and
   a gas backup module for a second operational mode and having an inlet for the additive gas, an integrated inlet for a gas for oxygenating said patient, a backup line, and an integrated backup outlet, the gas backup module being configured to add the additive gas to a patient in case of malfunction of delivery of additive gas from the gas administration module, wherein the inlet for the additive gas and the integrated inlet are connected to the backup line to mix the additive gas and the gas for oxygenating the patient to a set concentration of additive gas in the gas mixture at the integrated backup outlet.

2. The additive gas delivery apparatus according to claim 1, wherein the integrated backup outlet is connectable to a manual ventilation bag connectable to a patient connection.

3. The additive gas delivery apparatus according to claim 1, wherein the backup module comprises an actuator for switching between the first operational mode and the second operational mode, and wherein the actuator optionally is a mechanic actuator.

4. The additive gas delivery apparatus according to claim 1, comprising an integrated regulator for regulating a flow of the gas for oxygenation the patient within at least one predetermined range while the additive gas flow is constant.

5. The additive gas delivery apparatus according to claim 1, comprising a gas flow restrictor in an additive gas line between the first inlet and the backup gas line, the gas flow restrictor being controllable to set one of a plurality of predetermined gas flows of the additive gas.

6. The additive gas delivery apparatus according to claim 1, further comprising another integrated backup outlet connected to the inlet for the additive gas but not to the integrated inlet for the gas for oxygenating the patient to provide a flow of additive gas at the other integrated backup outlet.

7. The additive gas delivery apparatus according to claim 1, wherein a concentration of the additive gas at the integrated gas outlet is in the range of 1-40 ppm.

8. The additive gas delivery apparatus according to claim 1, wherein a concentration of the additive gas at the integrated gas outlet is in the range of 1-40 ppm.

* * * * *